United States Patent [19]

McCuen, II et al.

[11] Patent Number: 4,991,567
[45] Date of Patent: Feb. 12, 1991

[54] MICRO-IRIS RETRACTOR

[76] Inventors: Brooks W. McCuen, II, 2807 Montgomery St., Durham, N.C. 27705; Dyson Hickingbotham, 9805 Colt Dr., Bahama, N.C. 27503; Eugene de Juan, Jr., 2 Roswell Ct., Durham, N.C. 27707

[21] Appl. No.: 465,334

[22] Filed: Jan. 16, 1990

[51] Int. Cl.$^5$ ............... A61B 17/02; A61F 9/002/14
[52] U.S. Cl. .................... 128/20; 606/107; 606/151; 623/4
[58] Field of Search ............ 128/20; 606/1, 107, 606/138, 139, 166, 167, 151, 157, 158, 170, 171; 623/4-6

[56] References Cited

U.S. PATENT DOCUMENTS 3,659,607  5/1972  Banko ..................... 606/170 X
4,413,635 11/1983  Myer ...................... 606/151 X
4,712,550 12/1987  Sinnett ................... 606/151
4,777,950 10/1988  Kees, Jr. ................. 606/158
4,782,820 11/1988  Woods .................... 128/20

Primary Examiner—Ronald Frinks
Attorney, Agent, or Firm—Charles I. Brodsky

[57] ABSTRACT

This invention concerns the use of stainless steel, disposable tacks to be employed in the mechanical dilation of the iris during opthalmic surgery. Intended for temporary iris fixation, the tack is provided with a hook built onto its proximal end, and with a sharp anterior blade at its distal end. The anterior blade allows easy insertion of the tack through the peripheral cornea of the eye, at the limbal area, and an applicator is provided with a forked holder to firmly grasp the hook in securely placing and removing the tack in the surgical procedure.

9 Claims, 2 Drawing Sheets

MICRO-IRIS RETRACTOR

FIELD OF THE INVENTION

The present invention relates to the field of opthalmic surgery, in general, and to a tack to be employed in temporary iris fixation for cataract and posterior segment surgery, in particular.

BACKGROUND OF THE INVENTION

As is well known and understood, adequate dilation of the pupil of the eye is essential during cataract and posterior segment surgery. As is also understood, situations exist where the pupil cannot dilate adequately. For example, where there has been a prior surgical intervention, or where the eye has been traumatized, or where there exists a physiological reaction to a manipulation, various methods have been suggested to provide an adequate pupillary opening.

The simplest method involves the use of pharmaceuticals—but, in a significant number of patients, this arrangement often proves ineffective, and sometimes is associated with producing a toxicity to the cornea. A second method for enlarging the pupil is for the surgeon to excise a small wedge of the iris in an attempt to create an adequate pupillary aperture; however, such procedure (termed an "iridectomy") tends to produce an eccentric dilation—rather than a uniform one—and, additionally, releases pigment cells (because of the severance of the iris) which is preferable to avoid. A third method—i.e. mechanical dilation through a retraction of the iris by means of sutures passed through the scleral wall—has been noted to be delicate, time-consuming and awkward to accomplish.

SUMMARY OF THE INVENTION

As will become clear from the following description, the micro-iris retractor of the present invention avoids these limitations, and provides a temporary mechanical dilation in a simple, fast and inexpensive manner, requiring a decreased manipulation within the eye, and producing a reduced trauma to the sclera. As will be seen, the temporary iris fixation follows from the employment of a disposable, small stainless steel tack having a hook built into its proximal end. A sharp anterior blade is provided at the distal end of the tack, to allow for easy insertion through the peripheral cornea of the eye, at the limbal area. An applicator for the iris tack is also described, and in accordance with a preferred embodiment of the invention, is of a type consisting of a steel tube in which a fork holder (or forceps) is encased, to firmly secure the tack during placement, and retracting the tack during removal.

In a preferred usage of the iris tack of the invention, four retractors were noted to be placed (in the manner described below) within a mere two minutes, and providing a four-point retraction (either rectangular or square) for excellent visualization during the surgical intervention.

BRIEF DESCRIPTION OF THE DRAWINGS

These and other features of the invention will be more clearly understood from a consideration of the following description, taken in connection with the accompanying drawings, in which.

DETAILED DESCRIPTION OF THE DRAWINGS

Figure 1:
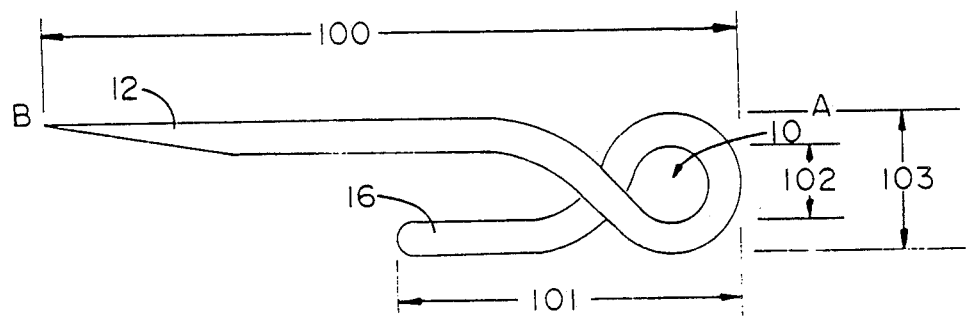
FIG. 1 shows an iris tack constructed in accordance with a preferred embodiment of the invention.

Referring to the tack of FIG. 1, is will be understood that reference numeral 10 identifies a hook-eyelet section built onto the proximal end of the tack (denoted by the designation A), with the tack being made of stainless steel. At the distal end B, a sharp, anterior blade 12 is shown, to permit easy insertion through the peripheral cornea of the eye at the limbal area (see FIGS. 4–6). So as to facilitate use of the tack in the opthalmic surgery procedures envisioned for pupil dilation, the following dimensions have been found to be particularly useful, with reference being had to FIG. 1, and with the understanding that all dimensions are measured in millimeters:

| Dimension 100 | 4.0 millimeters |
| Dimension 101 | 2.0 millimeters |
| Dimension 102 | 0.45 millimeters |
| Dimension 103 | 0.80 millimeters | and with the tack being fabricated of a stainless steel hardened wire of 0.20 millimeter diameter.

Figure 2:
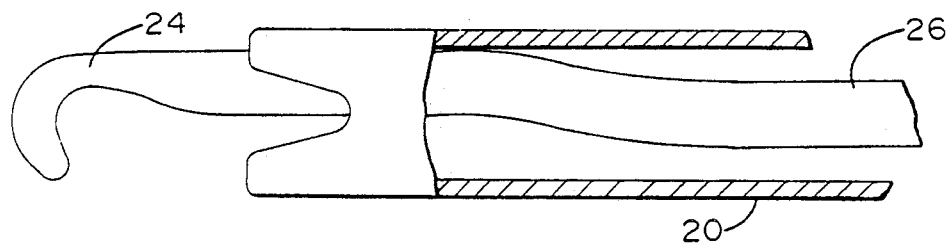
FIG. 2 shows a forceps to be employed with an actuator for placing and removing the iris tack in achieving a desired pupillary dilation.
Figure 3:
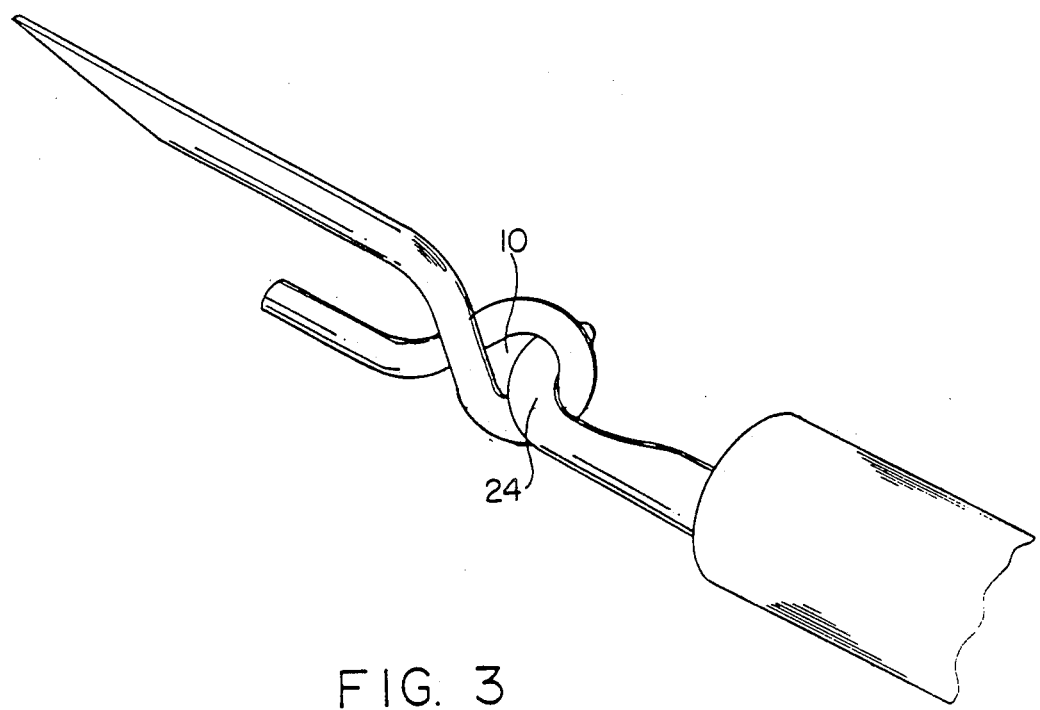
FIG. 3 illustrates how the forceps of FIG. 2 is actuated to grasp the iris tack of FIG. 1.

FIG. 2 shows an appropriate forceps for the iris tack, as extending through a stainless steel tube 20 of a typical 20 gauge thickness, with the tip end 24 arranged to insert into the hook-eyelet 10 of FIG. 1, and ready for actuation by means of a stainless steel wire connect 26 of some 0.350 millimeter diameter. As will be appreciated, the tip of the forceps 24 is arranged to pass through the eye 10 of the tack on a plane perpendicular to the metal eyelet 10 (FIG. 3) and with the forceps being of a spring loaded type as manufactured by Grieshaber & Co. A.G. of Schaffhausen, Switzerland, and identified as their Sutherland Rotatable Intraocular Micro Forceps. Such forceps are also available from their New York representative Grieshaber & Co., of 3000 Cabot Boulevard West, Langhorne, Penn. and operate by a pressure applied to a finger lever in a manner such that when the pusher is released, the hook portion 24 retracts to pull the eyelet 10 into the grooves and notches of the forceps to securely hold the tack in place.

Figure 4:
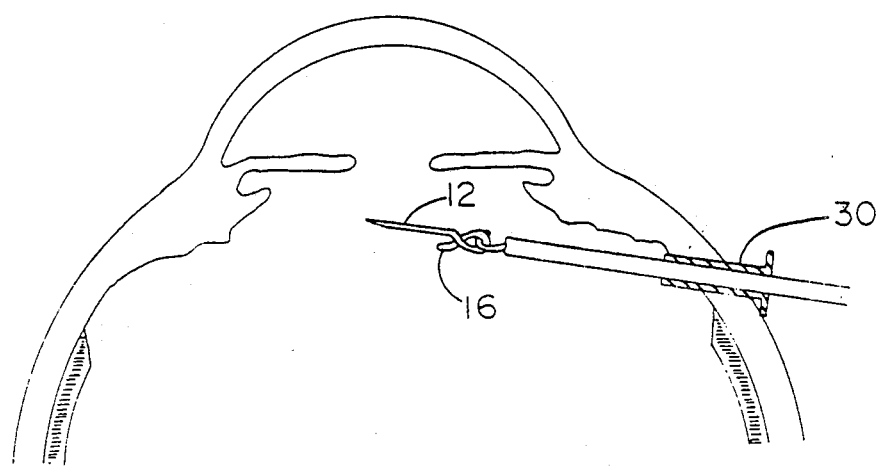
FIGS. 4–6 are helpful in an understanding of the method of inserting and removing the iris tack as part of the opthalmic surgerical procedure.
Figure 5:
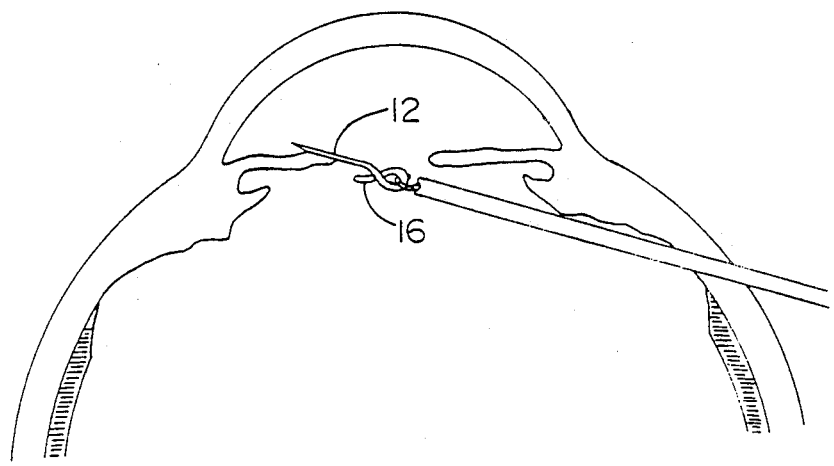
Figure 6:
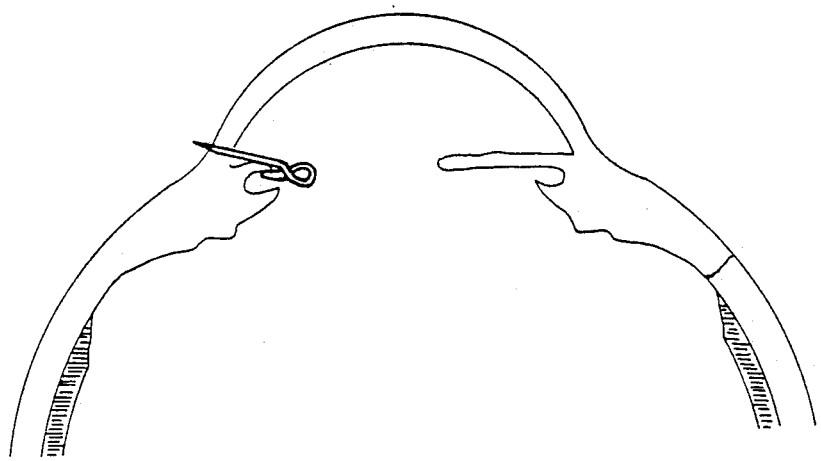

Referring now to FIGS. 4–6, it will be appreciated that the first step in the use of the micro-iris retractor of the invention is to depress the finger lever of the Grieshaber Sutherland Forceps (or other type arrangement) employed to expose the hook portion 24 (FIG. 2). The hook portion 24 is then inserted into the eyelet 10 of the iris tack, and the finger lever released so that the hook portion 24 retracts to grasp the tack for insertion. With the iris tack then secured at the hook portion 24, the surgical insertion is made at the sclerotomy site selected, preferably through a cannula 30, of 20 gauge (FIG. 4). With the anterior blade 12 of the tack being positioned posteriorly and beneath the iris, engagement of the iris then follows between the anterior blade 12 and the lower, rounded edge 16 of the tack extending from the hook-eyelet 10 (FIG. 5). Continuing the procedure, the iris is then retracted by inserting the anterior blade 12 into and through the scleral wall of the eye at the limbal area to firmly secure the tack during placement.

With the pupillary edge of the iris thus secured in this manner in the inferotemporal quadrant, the finger lever of the forceps is once again depressed to expose the hook portion 24 and release it from the tack (FIG. 6). With the iris tack then secured, a second tack is placed through the same sclerotomy and directed to fix the iris in position in like manner in the superonasal quadrant. A pair of tacks are thus placed anterior to the lens. Likewise, and in a similar manner,—it being understood that the first two iris tacks were emplaced from the superotemporal sclerotomy—a second pair of iris tacks are emplaced infertemporally and superotemporally by tacks applied from the superonasal sclerotomy. The fixation of the iris in these described four quadrants, using the conventional sclerotomies, thus produces a rectangular pupil which affords excellent dilation for work in the vitreous cavity, and particularly where the individual ones of the pairs of tacks are secured only several millimeters apart.

Again, as the finger lever is depressed, the hook portion 24 frees from, and may be slid from, the eyelet 10 and the forceps then may be removed.

As will be readily apparent, the secured tacks may be removed after the surgical procedure, in a similar, but reversed manner. At the conclusion of the procedure, with the iris tacks each removed, the pupil has been noted to rapidly return to its normal configuration postoperatively, with only a mild irregularly and residual enlargement being occasionally present. A widely dilated pupil was thus able to be obtained at the time of surgery, and with a postoperative return of the pupil to a near normal, preoperative configuration, without complications flowing from the use of the iris tacks.

As will be apparent to those skilled in the art, the micro-iris retractor arrangement described affords only a temporary use during a surgical procedure, and thus offers distinct advantages over the prior method of performing an iridectomy in which there is a permanent removal of the iris tissue and/or a severance of the pupillary sphincter. In comparison with the alternative method of retraction through the use of sutures, the desribed method with the micro-iris retractor is simpler, faster and requires less manipulation with the eye in use, while at the same time affording a decreased trauma to the sclera.

While there has been described what is considered to be a preferred embodiment of the present invention, it will be understood by those skilled in the art that modifications can be made without departing from the scope of the teachings herein. For example, although the iris tack of the invention has been described as being fabricated of stainless steel, it will be appreciated that alternative materials may be employed, such as a cobalt-/nickel/chromium/molybdenum/tungsten/iron alloy commonly referred to as "syntacoben". In like manner, other, alternative delivery systems might be envisioned—encompassing, perhaps, a modification of that portion of the tack which is grasped by the forceps, as well as a modification of the forceps employed so as to cooperate with the form of tack in securely placing into, or removing from, the iris margin. In this regard, it is to be understood, however, that so long as the pupil is fixed within the meridian of the tack—i.e. between the sharp anterior blade 12 and the shorter bearing edge 16—, the objectives of the invention will be satisfied. For at least such reasons, therefore, resort should be had to the claims appended hereto for a true understanding of the scope of the invention.

We claim:

1. Apparatus affording pupillary dilation for intraocular surgery, comprising:
    a tack for temporarily securing the iris in place during a surgical procedure;
    and an applicator, manually adjustable for grasping said tack and for releasing said tack, in the insertion of said tack into position and in its removal, as the case may be;
    and with said tack having an anterior blade and a bearing projection at a distal end, forming a meridian therebetween in which the iris is held in place when said tack is inserted into position in the eye.

2. The apparatus of claim 1 wherein said tack has an anterior blade, sharpened to facilitate insertion of said tack into the eye.

3. The apparatus of claim 1 wherein said applicator includes a lever, finger actuated to manually grasp said tack when said lever is released.

4. The apparatus of claim 1 wherein said tack includes an eyelet at a proximal end, grasped and released by said applicator in the insertion and removal of said tack when positioned.

5. The apparatus of claim 4 wherein said applicator includes a springloaded hook to manually grasp said eyelet in the insertion and removal of said tack.

6. The apparatus of claim 4 wherein said tack is fabricated of a continuous length of hardened metal, looped so as to form said eyelet and so that said anterior blade and bearing projection are formed and from the opposite ends of said continuous length.

7. The apparatus of claim 6 wherein said anterior blade extends a further distance towards the distal end of said tack than does said bearing projection.

8. The apparatus of claim 7 wherein said anterior blade is formed to a point to facilitate insertion into the eye, and wherein said bearing projection is formed of a rounded edge.

9. The apparatus of claim 6 wherein said tack is fabricated of stainless steel.

* * * * *